United States Patent [19]

Lai et al.

[11] Patent Number: 4,739,758

[45] Date of Patent: Apr. 26, 1988

[54] APPARATUS FOR STOMACH CAVITY REDUCTION

[75] Inventors: N. C. Joseph Lai, Brookfield; Wilfred Lynch, Racine, both of Wis.

[73] Assignee: Criticare Systems, Inc., Milwaukee, Wis.

[21] Appl. No.: 864,426

[22] Filed: May 19, 1986

[51] Int. Cl.$^4$ ............................................. A61M 29/02
[52] U.S. Cl. ................................. 128/303 R; 128/344
[58] Field of Search ........................... 128/303 R, 344; 604/265, 287

[56] References Cited

U.S. PATENT DOCUMENTS

| | | | |
|---|---|---|---|
| 2,508,690 | 5/1950 | Schmerl | 604/265 |
| 3,155,097 | 11/1964 | Barron | 604/265 |
| 3,736,939 | 6/1973 | Taylor | 604/265 |
| 4,249,535 | 2/1981 | Hargest | 604/265 X |

FOREIGN PATENT DOCUMENTS 3310234  9/1984  Fed. Rep. of Germany ... 128/303 R

*Primary Examiner*—Michael H. Thaler
*Attorney, Agent, or Firm*—Willian Brinks Olds Hofer Gilson & Lione Ltd.

[57] ABSTRACT

A method and apparatus for reducing the size of the stomach cavity in humans. A collapsed balloon is packaged in water soluble material and releasably attached to a filler tube. The balloon is inserted into the cavity through the mouth and esophagus and pumped up to a desired volume through the tube after water soluble material packaging has dissolved and the balloon deployed. After stomach fluids also dissolve the releasing mechanism, the filler tube is removed from the stomach. The balloon remains in the stomach for the required dieting time. Its volume prevents the usual ingestion of food into the stomach by obese patients, causing them to feel full, and reducing the desire for food. At the end of this period a puncturing mechanism is introduced into the stomach, punctures the balloon, grasps it and the balloon is removed through the esophagus and mouth.

3 Claims, 2 Drawing Sheets

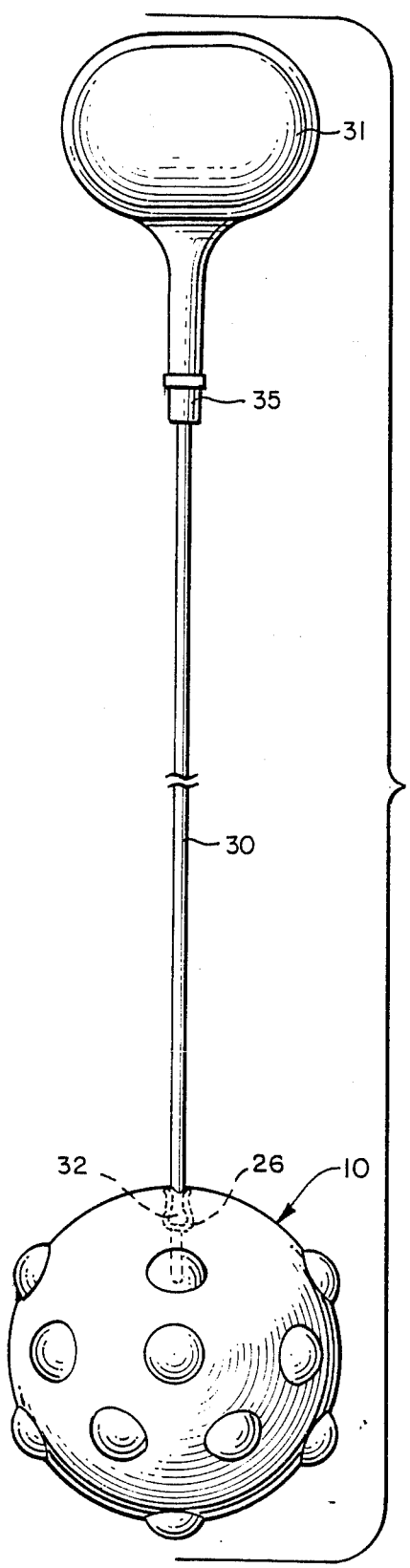
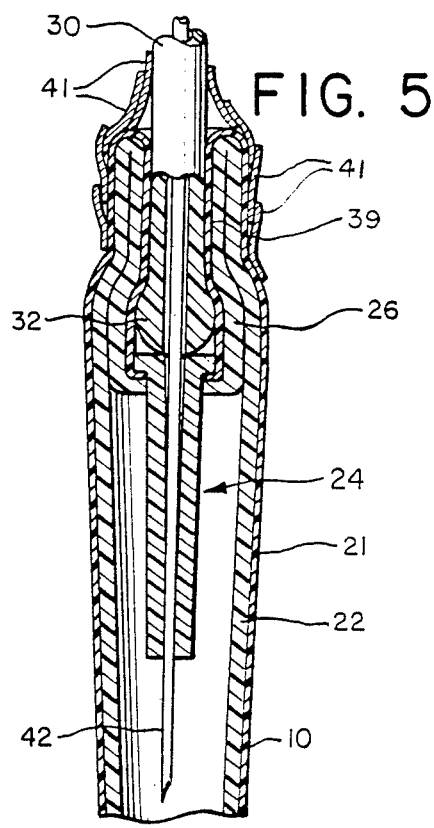
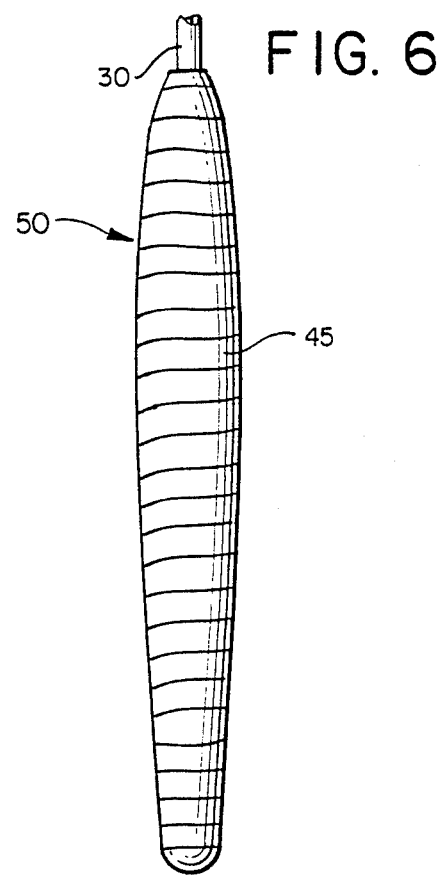

APPARATUS FOR STOMACH CAVITY REDUCTION

FIELD OF THE INVENTION

This invention relates in general to the medical treatment of obesity in human beings. It relates particularly to treatment by reduction in size of the stomach cavity.

BACKGROUND OF THE INVENTION

Inducing weight reduction in human beings by effectively reducing the size of the stomach cavity is not a new procedure. It has been accomplished in various ways, with varying degrees of difficulty, and with varying results.

For example, "stapling" of the stomach walls together along a line which reduces stomach cavity size is a well known surgical approach to combatting obesity. Since it involves surgery there is an element of danger, of course. It is also a relatively expensive procedure. Nevertheless, thousands of these operations are performed each year in the U.S. alone.

Another approach is disclosed in Berman et al. U.S. Pat. No. 4,133,315, issued Jan. 9, 1979, on a METHOD AND APPARATUS FOR REDUCING OBESITY. As described in this patent, stomach cavity size reduction is effected by inserting an inflatable bag or balloon into the patient's stomach through the esophagus, with an inflation tube extending out through the mouth. This device remains in place, according to the inventors, and can be inflated or deflated over a period of days or weeks to vary stomach cavity size as desired. When suitable results are achieved, the bag is removed through the esophagus with the inflation tube.

An improvement on the method disclosed in the Berman et al patent has also been practiced by Doctors Ole Gyring Nieben and Henrik Harboe at the University of Copenhagen's Hvidovre Hospital. Their approach has been to inflate a rubber balloon in the patient's stomach after inserting it in uniflated form through the esophagus. There the similarity to Berman et al. ends, however. The Nieben-Harboe method involves inflating the balloon with gas and then disconnecting the tube, withdrawing it from a valve on the balloon which closes automatically when the tube is pulled out. The balloon stays inflated for 7 to 21 days. When it collapses it passes out of the digestive track and is excreted.

SUMMARY OF THE INVENTION

It is an object of the present invention to provide an improvement on the Nieben-Harboe method of reducing stomach cavity size.

It is another object to provide a new and improved balloon construction for use in stomach cavity reduction treatment.

It is still another object to provide a new and improved balloon and balloon insertion tube assembly for use in stomach cavity reduction treatment.

The foregoing and other objects are realized in accordance with the present invention by providing a balloon which, when inflated, is generally spherical and measures approximately 2½ to 3 inches in diameter. The balloon skin is fabricated of inert material, preferably a copolymer such as Ethylene-Vinyl Acetate (EVA). A thin layer of silicone rubber may be bonded to the outer surface of the balloon to provide additional bio-compatibility with the patient.

The balloon has a substantial number of outwardly protruding blisters formed in it. These blisters provide an irregular periphery around the balloon which prevents the balloon from seating tightly against the cardia, or cardial orifice, and closing it. Similarly, the presence of these outwardly protruding blisters prevents the balloon from closing the stomach cavity opening, or the orifice into the duodenum.

The balloon is formed with an inverted inflation neck in an opening at what will be referred to as its top end. The inflation neck has a "duck-bill" valve extending inwardly from it, toward the center of the balloon. The neck is designed to receive and hold the flared tip of a filler tube. The valve functions as a check valve, permitting inflation of the balloon through the filler tube but preventing escape of gas from the balloon when the filler tube is removed.

The filler tube is a thirty inch section of thin, flexible, hollow tubing fabricated of DuPont Hytrel plastic or the like. The flared tip is formed at its lower end and a female Luer connection is mounted on its upper end.

With the filler tube tip seated in the inverted balloon neck a first thin strip of polyvinyl alcohol (PVA) plastic is moistened and wrapped snugly around the portion of the balloon surrounding the neck, the neck itself, and the flared filler tube tip. It seals the filler tube tip to the balloon.

A thin, plastic capillary tube longer than the filler tube is then inserted through it, from the Luer fitting end, into the collapsed balloon. This serves to permit any air still trapped in the collapsed balloon to escape as the balloon is packaged in the next operation.

At this point the balloon is rolled or folded tightly into a cigar-shaped package, axially aligned with the filler tube. After being moistened a second thin strip of PVA plastic is wrapped around the package, from one end to the other, to hold it in this tightly wrapped form. This second strip is also wrapped over the first strip of plastic. The capillary tube is removed.

In use, the PVA plastic strip wrapped package is inserted through a patient's mouth and esophagus into the stomach, the filler tube being used to effect insertion and, when the package has reached the stomach, still extending out of the patient's mouth. The PVA plastic is water soluble. Accordingly, the second strip begins to dissolve immediately upon being moistened in the patient's mouth. This causes the package to slide very easily into the stomach.

With the package in position in the patient's stomach, an air pump (syringe) or the like is seated in the Luer fitting. After two to five minutes the second strip of PVA plastic has been dissolved by moisture in the patient's stomach and the balloon is free to be deployed. Sensing when this occurs by applying pressure to the syring, the physician immediately inflates the balloon.

Meanwhile, the first strip of PVA plastic has begun to dissolve also. In another two to five minutes it has dissolved, releasing the filler tube tip. The filler tube can then be withdrawn from the patient. The inflated balloon remains in the patient's stomach.

In practice, the physician first X-rays the patient's stomach to determine the size balloon needed. The average inflated balloon size required would be 200 to 500 cubic centimeters.

After inroduction and inflation, the balloon might be left in place for 60 to several hundred days. The double wall material from which it is made will remain inflated indefinitely. When removal is desired, a flexible fiberoptic scope is inserted through the esophagus to locate the balloon in the stomach cavity. A conventional, multi-fingered gripping clamp coextensive with the scope is used to puncture the balloon and then grip it, after it has collapsed. Withdrawal of the scope and clamp withdraws the collapsed balloon from the patient through the esophagus.

BRIEF DESCRIPTION OF THE DRAWINGS

The invention, including the balloon and balloon insertion assembly, as well as the stomach reduction method in which they are used, are illustrated more or less diagrammatically in the drawings, in which:

FIG. 4 is an elevational view of the balloon and insertion assembly embodying features of the invention;

FIG. 5 is an enlarged sectional view of the connected filler tube and collapsed balloon; and FIG. 6 is an elevational view of a folded and wrapped balloon paackage as it would appear before being inserted into the stomach cavity.

DESCRIPTION OF THE PREFERRED EMBODIMENTS

Figure 1:
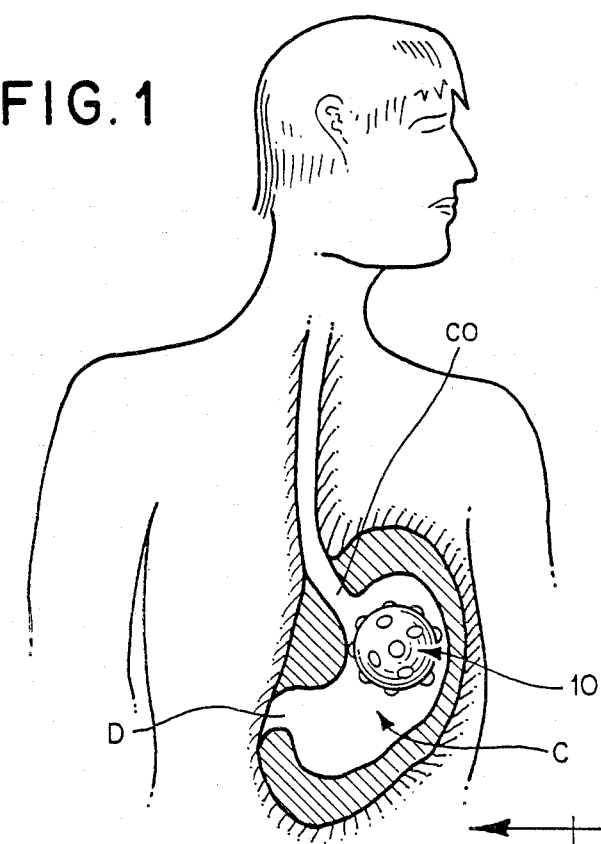
FIG. 1 is an elevational view of a stomach cavity reduction balloon embodying features of the present invention, with the balloon inflated in a patient's stomach.

Referring now to the drawings, and particularly to FIG. 1, an inflated stomach cavity reduction balloon embodying features of the invention is illustrated generally at 10, in a patient's stomach cavity C. The inflated balloon 10 occupies one-third or more of the available space in the stomach cavity C. The patient thus gets a "full" feeling much more quickly when eating and food intake is reduced dramatically. Weight reduction follows as a matter of course.

Figure 3:
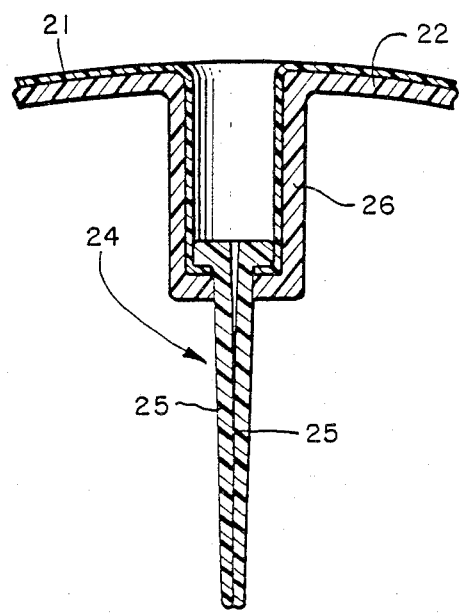
FIG. 3 is a sectional view taken along line 3—3 of FIG. 2.
Figure 2:
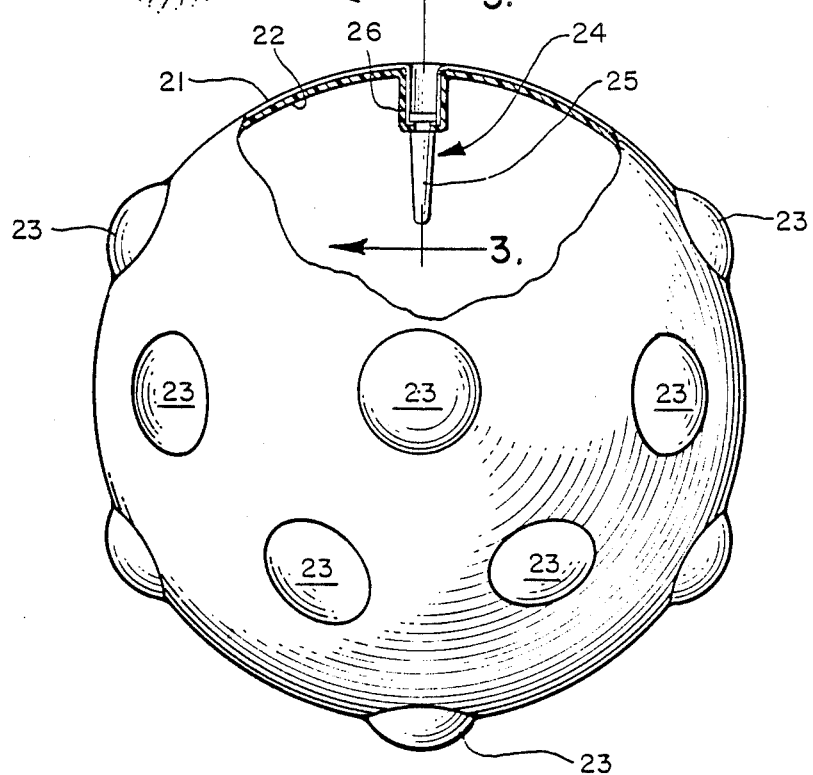
FIG. 2 is an enlarged elevational view of the inflated balloon of FIG. 1, with parts shown in section.

Referring now to FIGS. 2 and 3, it will be seen that the inflated balloon 10 is composed of two layers of material; the outer layer 21 being a thin (usually less than 0.001") film of silicone rubber and the inner layer 22 being a thicker film (about 0.005") of more durable, low gas permeable EVA, or other durable, low gas permeable polymer such as butyl or urethane. The inflated balloon 10 has many blisters 23 on its surface. These blisters 23 prevent the balloon 10 from seating tightly against the cardial orifice CO (see FIG. 1) and, accordingly, permit the safe passage of food past the orifice CO. The blisters 23 also permit the safe passage of digested food out of the stomach, around the balloon, through the duodenum opening D.

Formed in an opening in the top of the balloon 10 is an inverted neck 26, which extends into the balloon and has a conventional "duck-bill" valve 24 at its base. The lips 25 of the "duck-bill" valve 24 are pressed together by gas under pressure within the balloon 10 and prevent the escape of gas when the balloon is inflated. They open to permit the flow of gas into the balloon 10, however.

Referring now to FIG. 4, the balloon 10 is shown inflated but still connected to a filler tube 30 and a compressed air syringe 31. The tube 30 is ready to be withdrawn from the balloon neck 23 and the patient. The tube 30 is thirty inches long and is fabricated of a thermoplastic polymer such as DuPont Hytrel. It has a flared tip 32 which is seated snugly in the inverted balloon neck 26.

The tube 30 has a conventional female Luer lock 35 fitting mounted on its upper end. A conventional compressed air syringe 31 of predetermined capacity is releasably connected to the tube 30 by the Luer lock fitting 35. The balloon 10 has been inflated by compressing the air syringe 31 in a well known manner.

FIG. 5 is a further enlarged sectional view of the tube 30 and balloon 10, connected to each other prior to the balloon being inserted into the patient's stomach. The balloon 10 is collapsed at this point but has not yet been "packaged" for insertion.

As illustrated, the flared tip 32 of the filler tube 30 has been seated into the inverted neck 26 in the balloon 10. In this relationship, the balloon material forming a collar 39 around the opening into a neck 23 is pressed tightly against the tube 30 and a first strip 41 of water soluble PVA tape is wrapped tightly around the collar 39 and the tube 30, after being moistened to make it stick tightly to the collar, the tube, and itself. The tube 30 is, thus, sealed tightly to the balloon 10 with its flared tip 32 over the "duck-bill" valve 24.

At this point a plastic capillary tube 42 longer than the filler tube 30 is inserted through the latter into the collapsed balloon 10. The collapsed balloon is rolled or folded into a cigar-shaped package.

Referring now to FIG. 6, a second strip 45 of PVA plastic is then wrapped around the packaged balloon 10 after being moistened so that it sticks to the balloon, itself, and the first strip 41 of PVA plastic, which it covers. The capillary tube 42, through which entrapped gas has escaped during packaging, is now removed. The filler tube 30 and attached, packaged, balloon 10, form an assembly 50 embodying features of the invention.

The assembly 50 is used, according to the invention, by inserting the packaged balloon 10 through the patient's mouth and esophagus into the stomach S by manipulating the filler tube 30. The second strip 45 of PVA plastic immediately becomes slippery as it enters the mouth and begins to dissolve. After passing smoothly through the esophagus the packaged balloon 10 comes to rest in the stomach 10 and the fluids of the stomach react with the PVA tape 45 to fully dissolve it. Upon dissolution of the protective tape 45, the balloon 10 is free to inflate.

Air is pumped through the filler tube 30 and the duck-bill valve 24. After the desired volume of air has been pumped into the balloon, the physician needs to wait only for the stomach fluids to work on now unprotected first strip 41 of PVA plastic. As soon as the tape 41 is dissolved, usually after two to five minutes, the filler tube 40 is removed through the esophagus, leaving only the balloon 10 in the stomach.

When the desired dietary period has ended, a fiber optivc device is introduced to the patient's stomach through the mouth and esophagus. The device is equipped with a hook shaped tip which pierces the inflated balloon, causing it to deflate. The tip is manipulated by the physician to catch the wall of the deflated balloon and the balloon is pulled out of the patient's stomach, through the esophagus and mouth, easily and harmlessly.

The assembly 50 has been described as employing PVA plastic tape as its soluble binding element. It will be understood that other materials having substantially the same properties may be used. Examples are strips formed of hydroxylpropyl methylcellulose, sold under the trademark METHOCEL, or collagen.

While the preferred embodiment of the invention has been disclosed, it is understood that the invention is not limited to the disclosed example. Modifications in addition to those discussed can be made without departing from the invention. The scope of the invention is indicated in the appended claims, and all changes that come within the meaning and range of equivalency of the claims are therefore intended to be embraced therein.

We claim:

1. A balloon and balloon insertion and inflation assembly for use in stomach cavity reduction treatment, comprising:
   (a) a collapsed balloon for insertion through a patient's mouth and esophagus into the stomach cavity;
   (b) said balloon having an inflation neck with an opening therein and a check valve in said opening for preventing gas from escaping through said opening once said balloon is inflated;
   (c) tube means for introducing gas to said balloon through said opening and past said check valve to inflate said balloon;
   (d) said tube means being releasably connected to said neck by first water soluble material means;
   (e) said collapsed balloon being formed into a generally cigar-shaped package; and
   (f) second water soluble material means covering said cigar-shaped package and said first water soluble material means.

2. The assembly of claim 1 further characterized in that:
   (a) said first water soluble means is a strip of water soluble plastic material.

3. The assembly of claim 2 further characterized in that:
   (a) said second water soluble material is a strip of water soluble plastic material wrapped around said collapsed balloon and over said first water soluble material means.

* * * * *

UNITED STATES PATENT AND TRADEMARK OFFICE
CERTIFICATE OF CORRECTION

PATENT NO. : 4,739,758

DATED : April 26, 1988

INVENTOR(S) : N.C. Joseph Lai et al.

Page 1 of 2

It is certified that error appears in the above-identified patent and that said Letters Patent is hereby corrected as shown below:

IN THE BACKGROUND OF THE INVENTION

In column 1, line 41, please delete "uniflated" and substitute therefor --uninflated--.

IN THE SUMMARY OF THE INVENTION

In column 2, line 21, please delete "connection" and substitute therefor --connector--;

In column 2, line 55, please delete "syring" and substitute therefor --syringe--;

In column 2, line 65, please delete "inroduction" and substitute therefor --introduction--.

IN THE BRIEF DESCRIPTION OF THE DRAWINGS

In column 3, line 27, please delete "paackage" and substitute therefor --package--.

UNITED STATES PATENT AND TRADEMARK OFFICE
CERTIFICATE OF CORRECTION

PATENT NO. : 4,739,758
DATED : April 26, 1988
INVENTOR(S) : N.C. Joseph Lai et al.

It is certified that error appears in the above-identified patent and that said Letters Patent is hereby corrected as shown below:

IN THE DESCRIPTION OF
THE PREFERRED EMBODIMENTS

In column 4, line 17, please delete "into a" and substitute therefor --into the--;

In column 4, lines 56-57, please delete "fiber optivc" and substitute therefor --fiber optic--.

Signed and Sealed this

Twenty-ninth Day of November, 1988

Attest:

DONALD J. QUIGG

*Attesting Officer*    *Commissioner of Patents and Trademarks*